United States Patent [19]
Alsop

[11] 3,990,293
[45] Nov. 9, 1976

[54] METHOD AND APPARATUS FOR THE MEASUREMENT OF SURFACE TENSION

[75] Inventor: George Michael Alsop, South Charleston, W. Va.

[73] Assignee: Union Carbide Corporation, New York, N.Y.

[22] Filed: Dec. 12, 1975

[21] Appl. No.: 640,148

[52] U.S. Cl. .............................. 73/64.4; 73/61.1 R; 73/552
[51] Int. Cl.² ........................................ G01N 13/02
[58] Field of Search ............ 73/64.4, 61 R, 61.1 R, 73/552, 556, 69, 53; 23/230 R

[56] References Cited
UNITED STATES PATENTS

| | | | |
|---|---|---|---|
| 2,766,838 | 10/1956 | Shanley | 73/552 X |
| 3,381,525 | 5/1968 | Kartluke et al. | 73/53 X |
| 3,538,747 | 11/1970 | Munch | 73/53 |

Primary Examiner—Donald E. Watkins
Assistant Examiner—Joseph W. Roskos
Attorney, Agent, or Firm—Eugene Lieberstein

[57] ABSTRACT

The invention relates to methods and apparatus for the detection of changes in surface tension of a liquid by introducing an inert gas under pressure into the liquid to form an inert gas-liquid mixture, decompressing the mixture to provide bubbles which increase in size and generate sounds and measuring the sound intensity of the sound generated by the decompression of the gas-liquid mixture. Inasmuch as the addition of pollutants to water changes the surface tension characteristics of the water, the present invention is applicable to the monitoring of water for the detection of pollutants.

10 Claims, 2 Drawing Figures

METHOD AND APPARATUS FOR THE MEASUREMENT OF SURFACE TENSION

BACKGROUND OF THE INVENTION

1. Field of the Invention

The invention relates to the detection or monitoring of the surface tension of liquids and has particular application to the monitoring of liquids to detect the presence of pollutants. The addition of pollutants to water changes the surface tension of the water. The early detection of pollutants in liquids such as water has become highly important in recent years to aid in meeting state and national pure water requirements. The early detection of pollution caused by accidental spills and equipment failure is critically important in the attainment and continuance of pure water standards. In addition to being effective, pollutant detectors that are low in cost and simple to operate can be installed at many sample points where the high costs of other monitoring devices, e.g., total carbon analyzers have been prohibitive thereby multiplying the effectiveness of the detectors of this invention.

The present invention provides an effective, low cost, simple-to-operate, quick-acting method and device for continuously monitoring the surface tension of liquids and is especially useful in monitoring liquids such as water to detect the presence, if any, of pollutants therein. The method and apparatus of this invention involved the introduction of an inert gas under pressure into the liquid being monitored, decompressing the resulting gas-liquid mixture, and measuring the sound intensity of bubbles which form as a result of the decompression.

2. Description Of The Prior Art

Heretofore, sound intensity has been used to monitor gas-liquid systems by using listening devices to pick up the sound of gas bubbles breaking through the surface of a liquid. U.S. Pat. No. 2,766,838 describes a method of this type in monitoring reactions or changes taking place in solutions such as oxygen release from aqueous solutions of hydrogen peroxide, nitrogen and carbon dioxide release from aqueous solutions of sodium nitrite and urea by the addition of a mineral acid and carbon dioxide release from an aqueous sodium bicarbonate solution by the addition of mineral acid.

U.S. Pat. No. 2,614,645 uses a microphone, amplifier and loudspeaker for detecting the progress of chemical reactions in a reaction bomb.

Additionally, ultrasonic sound has been employed for inspecting and measuring various properties of liquids. U.S. Pat. No. 3,608,715 describes a method and apparatus for detecting particulate matter in liquids in closed containers using ultrasonic sound. U.S. Pat. No. 3,553,636 discloses a system for detecting liquid/liquid interface, viscosity and percent suspended solids in a liquid by utilizing ultrasonic sound.

Various systems and methods have been known heretofore for the determination of surface tension of liquids. U.S. Pat. No. 3,276,844 discloses a system and apparatus for controlling chemical reactions characterized by changes in the surface tension of the reacting mass as the reaction progresses. The system involves the continuous extraction of a sample of the reaction and measuring the pressure required to blow bubbles through the sample.

U.S. Pat. No. 3,854,324 describes a method and system for measuring the clotting time of blood by blowing a train of bubbles into it and detecting changes in the bubble formation characteristics by measuring changes in the pressure required to blow the bubbles.

U.S. Pat. No. 3,426,584 discloses a method and apparatus for measuring surface tension of a liquid by bubbling a gas through two tubes of different radii and placed at different depths in the liquid and measuring the difference in the pressure of flow in the two tubes.

U.S. Pat. No. 3,765,227 discloses apparatus for determining the surface tension of a liquid by measuring pressure differences of a gas in two tubes immersed in the liquid while blowing bubbles through one of the tubes.

U.S. Pat. No. 3,555,783 relates to a method and apparatus for dissolving a gas in a liquid at pressures greater than atmospheric.

None of the above patents, however, relate to a method or apparatus for detecting changes in the surface tension of a liquid or for detecting pollution in a liquid involving the introduction into the liquid of an inert gas under pressure, decompressing the resulting gas-liquid mixture and measuring the sound intensity of bubbles increasing in size during decompression.

SUMMARY OF THE INVENTION

The present invention is based in part on the discovery that changes in the surface tension of liquids can be detected by changes in the intensity of sound created by bubbles as they form in the liquid when it is decompressed. In addition, the invention is based on the discovery that pollutants when added to water change the surface tension of the water.

This invention provides a method and apparatus for monitoring liquids and detecting changes in the surface tension thereof. Unlike classical surface tension measurements, the method and apparatus of this invention monitor the sound intensity created by bubbles as they form in a decompression chamber. In the present invention, a stream of the liquid being measured is saturated with an inert gas under pressure. The resulting gas-liquid mixture is decompressed and gas bubbles are formed the size of which is dependent on the surface tension of the liquid. The size of bubbles created when pressure is released from water that has been previously saturated with a gas under pressure is a function of surface tension which is altered by the presence of organic contaminants. The larger bubbles create a higher sound intensity than do the smaller bubbles.

The sound created by the bubbles forming in the liquid under decompression is picked up by a microphone or other transducer the output of which is fed to a voltmeter, oscilloscope or other signal measuring and display or recording device.

The method and apparatus of this invention are reliable, accurate, quick-acting, easy to operate and low in cost. They can be employed on a continuous basis to measure a flowing sample stream of the liquid and are especially applicable to monitoring water for the presence of pollutants. The method and apparatus of this invention have excellent sensitivity for a wide range of types of pollutants in water and can detect the presence of pollutants in concentrations of less than 100 mg/l (ppm). The apparatus of this invention is low in cost and can be installed at many sample points whereas the high cost of other monitoring devices, e.g., total carbon analyzers have prohibited the use of heretofore known monitoring devices on an extensive basis.

The method and apparatus of this invention detect changes in the surface tension of liquids by introducing a gas under pressure into the liquid to form a gas-liquid mixture, subjecting the mixture to decompression to provide bubbles in the liquid and generate sound which is characteristic of the size of the bubbles and the surface tension of the liquid, and measuring the intensity of sound generated by decompression of the mixture.

DESCRIPTION OF A PREFERRED EMBODIMENT

Figure 1:
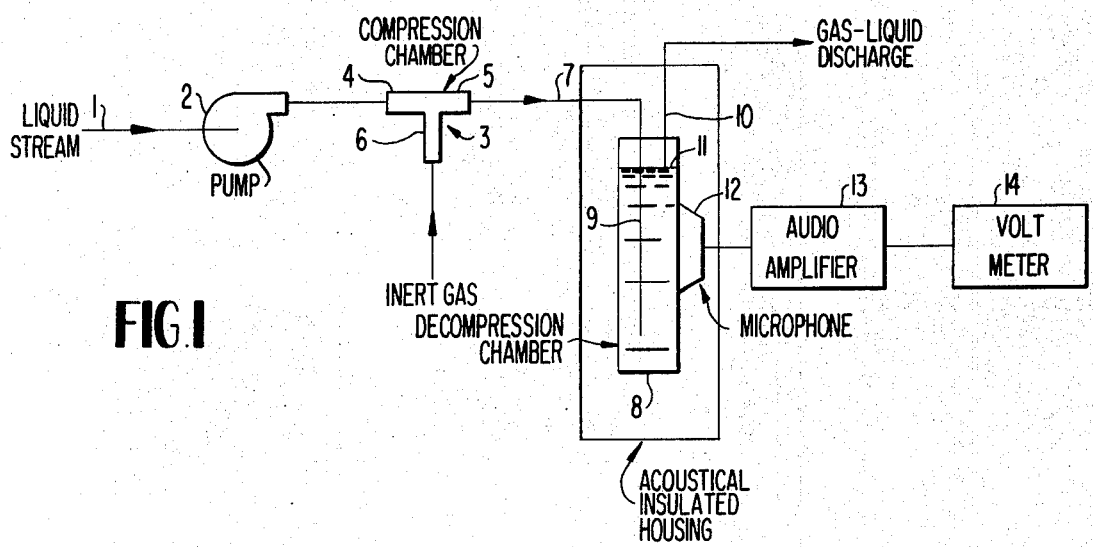
FIG. 1 is a diagrammatic view partly in section of an embodiment of this invention.

Referring to FIG. 1, a liquid stream entering through line 1 which is connected to a source of said liquid, e.g., an effluent waste stream, cooling water effluent, etc., passes through pump 2 which pumps it into compression chamber 3 which is in the form of a "Tee" connection having arms 4 and 5 and leg 6 perpendicular thereto. The pipe 1 is connected to arm 4. Arm 5 is connected to line 7 and leg 6 is connected to a source of pressurized inert gas for delivering said gas to the compression chamber 3.

Decompression chamber 8 is provided with an inlet tube 9 extended to a point near the bottom of said chamber and is open at said point to deliver liquid to the chamber. Decompression chamber 8 is also provided with a discharge tube 10 extending to a point near the top of said chamber and is open at said point to receive the contents of the chamber and deliver same to a zone of pressure lower than that in compression chamber 3, for example, to atmospheric pressure. The liquid level in decompression chamber 8 is indicated by numeral 11.

A microphone 12 is placed against decompression chamber 8 to receive sounds from said chamber. The microphone 12 is operatively connected to an audio amplifier 13 to deliver thereto signals representative of the intensity of sound picked up by said microphone. An AC voltmeter 14 is connected to the output of the amplifier 13 and measures and displays and/or records the peak-to-peak voltage output of said amplifier. An acoustically insulated housing 15 is provided around the decompression chamber 8 and microphone 12 to isolate them from external noise.

In operation, the liquid to be monitored is continuously pumped into compression chamber 3 through arm 4 and inert gas under pressure is continuously supplied to said chamber through leg 6. A gas-liquid mixture is formed in compression chamber 3 and continuously passes through line 7 to inlet tube 9 into decompression chamber 8. When the liquid level in decompression chamber 8 reaches the lower open end of discharge tube 10, i.e., level 11, it enters said tube and is discharged to a zone of pressure lower than that found in compression chamber 3. The zone of lower pressure is conveniently atmospheric pressure. The discharge from tube 10 is directed to the drain or is otherwise suitably disposed of.

With the liquid level at point 11 in the decompression chamber 8 voltage readings on voltmeter 14 are observed and recorded, if desired. The apparatus described can be maintained in continuous operation to continuously monitor the liquid from the source stream. It is of simple design and requires very little or no maintenance or repair even when operated over extremely long periods. The only material consumed in the operation of the apparatus is the inert gas and this is consumed at a very low rate. Any gas that does not chemically react with the liquid being monitored can be used and this is what is meant by the term "inert gas". From the standpoints of economy and availability nitrogen gas probably is the most practical. Nitrogen gas is readily available from cylinders of liquid nitrogen and is inexpensive compared to other liquefied gases. Nevertheless, other inert gases are operative including the expensive rare gases such as argon, xenon, neon, etc. Compressed gases such as compressed air from a compressed air tank or a compressor can be used. LNG, liquid propane, liquid butane will function in the apparatus but can present serious fire hazards. There may be instances in which chlorine or carbon dioxide would be useful in the method and apparatus of this invention.

The pressures employed in the compression chamber 3 and decompression chamber 8 are not critical so long as there is a sufficient differential to result in bubble formation in the decompression chamber 8. For example, the pressure in the compression chamber 3 could be atmospheric or slightly above or below, if the decompression chamber 8 were at sub-atmospheric pressure which could be achieved by connecting discharge tube 10 to vacuum, although in most cases this would appear to be a difficult way to achieve the results of this invention. Pressure of the liquid coming into the compression chamber 3 is conveniently consistent with the desired flow rate through the apparatus. Rapid flow rates provide faster detection and are usually desired. Representative pressures of the incoming liquid in line 1 fall in the range of 10 to 50 p.s.i.g. and representative of pressures of inert gas entering through leg 6 are 15 to 60 p.s.i.g. Pressures above and below these ranges can be employed, the criterion being that bubbles should form in the decompression chamber 8. It is also advantageous that the pressure of incoming inert gas be higher than that of the liquid entering compression chamber 3, in order to enhance mixing of the gas and liquid. However, the criterion is to achieve mixing of the gas in the liquid to an extent that bubbles form in the decompression chamber 8 under the existing conditions.

The apparatus described in FIG. 1 was used to test water and various contaminants in water as listed in Table 1 below. In each instance, the incoming water, or water contaminated with the organic materials listed in Table 1, was at a pressure of 25 p.s.i.g. as it entered arm 4. Nitrogen from a tank of liquid nitrogen was used as an inert gas and it entered leg 6 at a pressure of 30 p.s.i.g. Discharge tube 10 is opened to ambient atmospheric pressure.

Table 1 lists each organic material tested, its concentration in water in mg/1 (ppm) and the output peak-to-peak voltage measured by the voltmeter 14.

TABLE 1

| COMPOUND | CONCENTRATION, mg/l | OUTPUT VOLTAGE |
|---|---|---|
| Water | — | 8.0 |
| Vinyl Triethyoxy- | 118 | 1.0 |

TABLE 1-continued

| COMPOUND | CONCENTRATION, mg/l | OUTPUT VOLTAGE |
|---|---|---|
| silane | | |
| Acetone | 105 | 5.8 |
| | 1050 | 1.5 |
| Acrylonitrile | 107 | 7.5 |
| Acrylic Acid | 138 | 2.5 |
| Amyl Alcohol | 25 | 1.2 |
| Butyl Carbitol | 126 | 0.8 |
| n-Butanol | 107 | 0.8 |
| n-Butylamine | 98 | 2.5 |
| 1,4-Butanediol | 135 | 5.0 |
| Butyl Cellosolve Acetate | 124 | 0.2 |
| n-Butyl Chloride | 118 | 7.8 |
| Benzyl Alcohol | 138 | 7.0 |
| Carbowax* 750 | 132 | 0.2 |
| Carbowax* 600 | 132 | 0.5 |
| Cyclohexanone | 125 | 1.8 |
| Crotonaldehyde | 113 | 1.5 |
| Carbitol Acetate | 134 | 0.1 |
| Caprolactone | 132 | 0.8 |
| $C_{11}$-$C_{13}$ Alcohols | 132 | 7.8 |
| 1,4-Dioxane | 137 | 6.8 |
| | 137 | 6.0 |
| Diethylene Glycol | 148 | 7.5 |
| | 888 | 1.0 |
| Diacetone Alcohol | 124 | 1.5 |
| Decanol | SAT. | 7.0 |
| Epichlorohydrin | 155 | 7.0 |
| Ethyl Butyl Ketone | 132 | 0.8 |
| 2-Ethylhexanol | 120 | 7.5 |
| Ethyl Acetate | 119 | 5.5 |
| | 715 | 1.5 |
| Ethyl Acrylate | 122 | 2.8 |
| Ethylamine | 92 | 7.0 |
| 2-Ethylhexanoic Acid | 120 | 1.5 |
| n-Ethyl Morpholine | 121 | 0.8 |
| Ethanol | 627 | 1.2 |
| 2-Ethylhexaldehyde | 108 | 7.5 |
| Hexylene Glycol Diacetate | 132 | 0.2 |
| n-Hexane | 87 | 7.5 |
| Isobutyronitrile | 102 | 7.0 |
| Isophorone | 122 | 0 |
| Isopropanol | 104 | 3.2 |
| | 624 | 2.5 |
| 2-Ethyl-5-Methyl Pyridine | 132 | 0.8 |
| Methyl Acetate | 124 | 6.5 |
| | 744 | 5.0 |
| Methanol | 105 | 6.0 |
| | 630 | 2.5 |
| | 1050 | 1.8 |
| Niax** Polyol 14-46 | 132 | 6.5 |
| Di-n-Propylamine | 98 | 0.8 |
| Pyridine | 130 | 5.5 |
| Tetralin | SAT. | 8.2 |
| Ucon* 50-HB-100 | 132 | 0.4 |
| Ucon* 50-HB-170 | 132 | 0.5 |
| Ucon* 50-HB-260 | 132 | 0.2 |
| Ucon* 50-HB-5100 | 132 | 0 |
| Valeric Acid | 124 | 0.2 |

*Trademark of Union Carbide designating polyoxyalkylene compositions of relatively high molecular weight.
**Trademark of Union Carbide Corporation designating polymeric polyol compositions.

In order to demonstrate that suspended solids in the liquid has very little, if any, effect on the operation of the method and apparatus of this invention, various amounts of solids (talc) as listed in Table 2 below were added to and suspended in water and water contaminated with various amounts of organic materials as listed below. The water and contaminated water with and without suspended solids were tested in the apparatus shown in FIG. 1 using an inlet pressure at arm 4 of about 25 p.s.i.g. and nitrogen gas at a pressure at leg 6 of about 30 p.s.i.g. Measurements of peak-to-peak output voltage were read on voltmeter 14 and are listed in Table 2. These results show that even large amounts of suspended solids have very little, if any, effect on the monitoring and detection of contaminants in water by the method and apparatus of this invention.

TABLE 2

| COMPOUND | SOLIDS, mg/l | OUTPUT VOLTAGE |
|---|---|---|
| Acrylic Acid at 138 mg/l | None | 2.0 |
| | 100 | 2.0 |
| | 1000 | 1.5 |
| | 10,000 | 1.5 |
| Carbowax* 600 at 132 mg/l | None | 0.4 |
| | 100 | 0.5 |
| | 1000 | 0.4 |
| Water | None | 8.0 |
| Water | 10,000 | 8.0 |

*Trademark of Union Carbide designating solid water-soluble polyethylene glycols.

In order to demonstrate that the method and apparatus of this invention can perform satisfactorily under a wide range of temperature conditions of the liquid or water being monitored, water contaminated with organic materials at various temperatures as listed in Table 3 below were tested in the apparatus shown in FIG. 1 using an inlet pressure at arm 4 of about 25 p.s.i.g. and a nitrogen gas pressure at leg 6 of about 30 p.s.i.g. Measurements of peak-to-peak voltages were taken from voltmeter 14 and are recorded in Table 3 below. These results show that the method and apparatus of this invention is fully operative over a wide range of temperatures which might be expected to be encountered in use.

TABLE 3

| COMPOUND | TEMPERATURE, °C | OUTPUT VOLTAGE |
|---|---|---|
| Carbitol Acetate 134 mg/l | 17 | 0.5 |
| | 65 | 1.8 |
| 2-Ethylhexanoic Acid 120 mg/l | 14 | 0.8 |
| | 69 | 1.5 |

Figure 2:
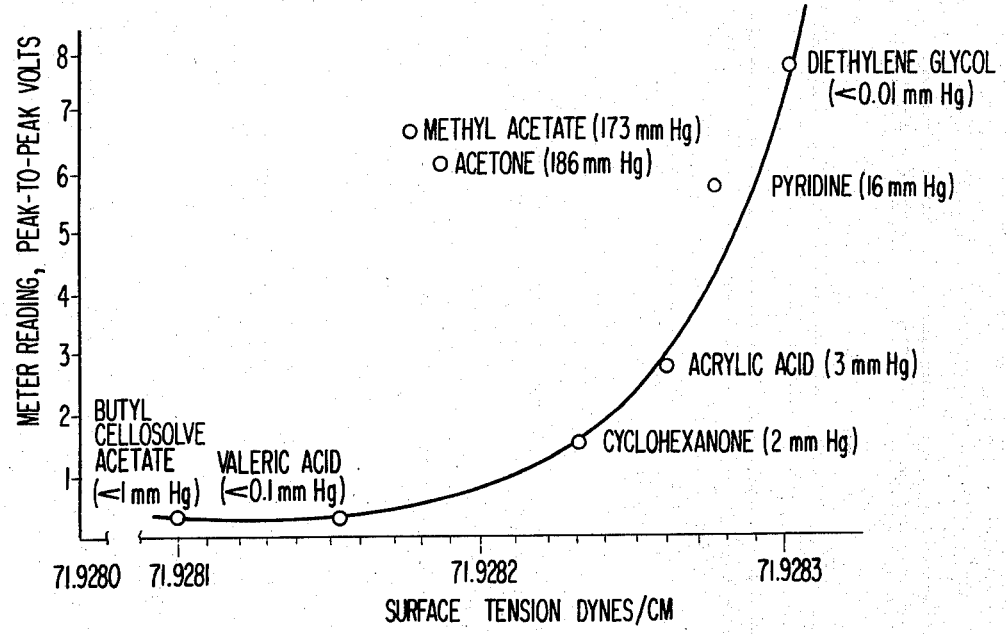
FIG. 2 is a graph of peak-to-peak voltage as measured by the apparatus and method of the present invention to water contaminated by the organic compound shown in the graph versus surface tension in dynes per centimeter calculated for the contaminated water in each case.

The apparatus and method of this invention are able to sense or detect the presence of water of very minute amounts of contaminants having low vapor pressures. This is shown in FIG. 2 wherein there are plotted peak-to-peak voltage readings from voltmeter 14 obtained by testing water contaminated with the organic materials listed in FIG. 2 using the corresponding amounts and conditions used for the tests reported in Table 1 in the less than 200 mg/l range of concentrations. Also plotted are the surface tensions in dynes per centimeter calculated for each tested contaminated water by assuming ideal solutions and adding the proportional amount of surface tension contributed by each component based on mole fractions.

The vapor pressure at 20° C. for each organic contaminant tested is given in FIG. 2. The results given in FIG. 2 indicate that the apparatus and method of this invention are generally highly sensitive in detecting small amounts of contaminants having a relatively low vapor pressure and a relatively low calculated surface tension. It also indicates that contaminants of appreciably higher vapor pressure such as acetone or methyl acetate are somewhat less sensitive to detection than would be predicted from calculated surface tension and may be somewhat more difficult to detect. The method and apparatus of this invention nevertheless are fully capable of detecting the presence of contaminants which result in a peak-to-peak voltage which is discernibly different from that of water.

What is claimed is:

1. Method of detecting changes in the surface tension of a liquid comprising the steps of introducing an inert gas under pressure into the liquid to form an inert gas-liquid mixture, decompressing said mixture to provide bubbles which increase in size and generate sound, and measuring the sound intensity of said sound generated by decompression of said inert gas-liquid mixture.

2. Method as claimed in claim 1 wherein said liquid is predominantly water.

3. Method as claimed in claim 1 wherein said inert gas is nitrogen.

4. Method as claimed in claim 1 wherein said steps are carried out continuously.

5. Method of detecting water pollution in a body of water comprising the steps of injecting under pressure an inert gas into a sample of said body of water to form an inert gas-water mixture, decompressing said mixture to generate bubbles that increase in size and generate sound, measuring the intensity of said sound generated by decompression of said inert gas-water mixture and correlating said sound intensity with that of substantially pure water to determine the presence or absence of contamination of said water.

6. Apparatus for detecting changes in the surface tension of a liquid due to the presence of foreign material comprising in combination a compression chamber to which said liquid is fed, means for introducing an inert gas under pressure into said liquid in said compression chamber to form an inert gas-liquid mixture, a decompression chamber connected to said compression chamber and to which said inert gas-liquid mixture is fed and decompressed, and a microphone operatively connected to said decompression chamber to sense the intensity of sounds originating within said decompression chamber.

7. Apparatus as claimed in claim 6 wherein said decompression chamber and microphone are covered with acoustical insulation to dampen external sounds.

8. Apparatus as claimed in claim 6 which includes an audio amplifier operatively connected to said microphone to receive and amplify the output of said microphone and a voltmeter operatively connected to said audio amplifier to receive and measure the output peak-to-peak voltage of said audio amplifier.

9. Apparatus as claimed in claim 6 wherein said decompression chamber has an inlet in the lower portions thereof said inlet being connected to said compression chamber to receive said gas-liquid mixture therefrom and an outlet in the upper portions thereof said outlet being connected to a zone of lower pressure than the pressure in said compression chamber and discharging decompressed gas-liquid mixture from said decompression chamber.

10. Apparatus as claimed in claim 6 wherein said compression chamber is a tee pipe connector having two aligned arms and a single leg perpendicular thereto and in which one arm is connected to a source of said liquid, the other arm is connected to said decompression chamber and the single leg is connected to a source of said inert gas.

* * * * *